(12) United States Patent
Zhang et al.

(10) Patent No.: US 11,680,884 B2
(45) Date of Patent: Jun. 20, 2023

(54) APPARATUS AND A METHOD FOR TESTING WATER ABSORPTION OF CONCRETE IN A DIRECTION PARALLEL WITH A LOAD APPLYING DIRECTION

(71) Applicant: QINGDAO UNIVERSITY OF TECHNOLOGY, Qingdao (CN)

(72) Inventors: Peng Zhang, Qingdao (CN); Jiuwen Bao, Qingdao (CN); Shuguo Li, Qingdao (CN); Tiejun Zhao, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 419 days.

(21) Appl. No.: 17/057,909

(22) PCT Filed: Feb. 14, 2020

(86) PCT No.: PCT/CN2020/075302
§ 371 (c)(1),
(2) Date: Nov. 23, 2020

(87) PCT Pub. No.: WO2020/192295
PCT Pub. Date: Oct. 1, 2020

(65) Prior Publication Data
US 2021/0372900 A1 Dec. 2, 2021

(30) Foreign Application Priority Data
Mar. 28, 2019 (CN) .......................... 201910242193.4

(51) Int. Cl.
*G01N 5/02* (2006.01)
*G01N 3/08* (2006.01)
(Continued)

(52) U.S. Cl.
CPC .................. *G01N 5/02* (2013.01); *G01N 3/08* (2013.01); *G01N 3/16* (2013.01); *G01N 33/383* (2013.01);
(Continued)

(58) Field of Classification Search
CPC ............ G01N 5/02; G01N 5/025; G01N 3/08; G01N 3/16; G01N 33/383; G01N 2203/0019; G01N 2203/0037
See application file for complete search history.

(56) References Cited

U.S. PATENT DOCUMENTS

| 6,658,921 B2 * | 12/2003 | Lavallee | ................ G01N 33/42 177/50 |
| 2002/0162387 A1 * | 11/2002 | Lavallee | ............ G01N 15/0893 73/73 |
| 2019/0212318 A1 * | 7/2019 | Tang | ......................... B01L 5/00 |

FOREIGN PATENT DOCUMENTS

| CN | 101074912 A | 11/2007 |
| CN | 103471953 A | 12/2013 |

(Continued)

OTHER PUBLICATIONS

ISR. PCT/CN2020/075302, PCT Search Report and Written Opinion dated Apr. 28, 2020, with translation, China National Intellectual Property Administration (9 pgs).

*Primary Examiner* — Jonathan M Dunlap
(74) *Attorney, Agent, or Firm* — Meunier Carlin & Curfman LLC

(57) ABSTRACT

An apparatus and a method for testing water absorption of concrete in a direction parallel with load applying direction are provided. The apparatus includes a loading device, a water filling device, and a monitoring device. The loading device includes an upper support plate and a lower support plate connected with the upper support plate via multiple threaded rods, and a space for placing a concrete specimen formed between the upper support plate and the lower support plate. The water filling device includes a water filling cylinder having a side connected with a water supply tank via an inlet pipe, and another side connected with a water storage tank via an outlet pipe. The monitoring device (Continued)

includes a mass sensor arranged under the water storage tank and a strain gauge for detecting change of stress of the concrete specimen.

17 Claims, 2 Drawing Sheets

(51) Int. Cl.
  *G01N 3/16* (2006.01)
  *G01N 33/38* (2006.01)
(52) U.S. Cl.
  CPC .............. *G01N 2203/0019* (2013.01); *G01N 2203/0037* (2013.01)

(56) References Cited

FOREIGN PATENT DOCUMENTS

| | | | | |
|---|---|---|---|---|
| CN | 206387699 U | | 8/2017 | |
| CN | 206593998 U | | 10/2017 | |
| CN | 107607428 A | | 1/2018 | |
| CN | 206891906 U | | 1/2018 | |
| CN | 105716989 B | * | 10/2018 | ......... G01N 15/0806 |
| CN | 108801833 A | * | 11/2018 | |
| CN | 208206743 U | | 12/2018 | |
| CN | 109813626 A | | 5/2019 | |
| CN | 108132206 B | | 1/2020 | |

* cited by examiner

APPARATUS AND A METHOD FOR TESTING WATER ABSORPTION OF CONCRETE IN A DIRECTION PARALLEL WITH A LOAD APPLYING DIRECTION

TECHNICAL FIELD

The present disclosure relates to a field of detecting durability of concrete material, and in particular to an apparatus and a method for testing water absorption of concrete in a direction parallel with load applying direction.

BACKGROUND ART

In a process of servicing, the concrete undergoes erosion of chloride salts, freeze-thaw, and carbonization, and the deterioration process thereof may be accelerated due to wind, vehicle, and wave, causing the concrete to crack or peel off. The micro-cracks generated by the load have a significant impact on the durability of the concrete structure. The degradation of performance of the concrete will be accelerated under the dual action of the micro-crack and the service environment. In addition, the existence and transmission of moisture is an indispensable key factor for the many degradation problems of durability of concrete materials. The moisture and harmful medium carried thereby intrude into the interior of the concrete by capillary action, resulting in a series of physical and chemical reactions, which leads to a reduction in the bearing capacity of concrete structure and greatly reduces the service life of the structure. Currently, water absorption is widely used to evaluate the water absorbing characteristics of building materials, which is served as an important indicator for describing the durability of building materials. However, a direction of the load may affect a transmission process of the moisture and determine a transmission rate of the moisture.

There are many existing apparatuses for testing water absorption rate of concrete. An apparatus for testing water absorption rate of recycled sandless concrete with multi-pore is disclosed by Chinese patent NO. 201810127829.6. The apparatus includes a weighing device provided with a cylindrical container. A water delivery pipe is placed above the cylindrical container and is equipped with a holder. Another end of the water delivery pipe is connected with a container bottle fixedly connected with a weighing sensor. The weighing sensor is connected with a computer via a wire and is fixedly mounted on the upper of an upright tube. A triangle bracket is equipped on the bottom of the upright tube. A sample zone is provided in middle of the cylindrical container. A bottom of the cylindrical container is located below the sample zone. A second sensor is provided at A2 above the sample zone and a third sensor is provided at A3, where A3 is located in a range of the sample zone below A2. A first sensor is provided at A1 above A2. The first sensor, the second sensor and the third sensor are connected with a analog-to-digital converter via wires. The first sensor, the second sensor, and the third sensor are connected to each other in parallel. The analog-to-digital converter is connected with a processor via a wire. The processor is connected with a buzzer via a wire in one side and is connected with the wireless data transmitter via a wire in another side. A wireless data receiver is connected with the data processor via a wire. The data processor is connected with a controller via a wire. The controller is connected with a first resistor via a wire, which is connected with a triode via a wire. The triode includes a base, a collector and an emitter. The collector is connected with a second resistor via a wire. An electromagnetic induction device is equipped in the holder. The collector is connected with a terminal C1 of the electromagnetic induction device via a wire. The controller and the emitter are connected with a terminal C2 of the electromagnetic induction device via wires. The electromagnetic induction device includes a coil iron core. The coil iron core is surrounded by an enamelled wire coil. A first spring is equipped on one side of the electromagnetic induction device and a second spring is equipped on another side of the electromagnetic induction device. A first metal piece is mounted on an inner wall of the holder corresponding to one end of the electromagnetic induction device. A second metal piece is mounted on an inner wall of the holder corresponding to another end of the electromagnetic induction device. A holder upper port and a holder lower port are equipped on another side of the second spring.

A monitoring system for monitoring a water absorption rate of concrete material in real time is disclosed by Chinese patent NO. 201710698341.4, which includes a water absorption monitoring device and a water evaporation monitoring device. The water absorption monitoring device includes a fixed end, a rope, a water storage container I, a net bag, a test material, an electronic balance I and a monitoring device I. The rope has an upper end connected with the fixed end and a lower end connected with the net bag. The net bag is located in the water storage container I. The test material is installed in the net bag. The water storage container I is placed on the electronic balance I. The monitoring device I is configured to continuously record the changes of the display result of the electronic balance I. The water evaporation monitoring device includes an inlet pipe, a water storage container II, an electronic balance II and a monitoring device II. The inlet pipe is arranged above the water storage container II. The water storage container II is placed on the electronic balance II. The monitoring device II is configured to continuously record the change of the display result of the electronic balance II.

An instrument for testing water absorption rate of a surface of concrete is disclosed by Chinese patent NO. 201720610281.1, which includes a test water tank, an inlet pipe, a control valve, a water level gauge, an upright, a clamping device and a position sensor. The inlet pipe is fixedly mounted at a side wall of a lower end of the test water tank. The control valve is fixedly mounted on the inlet pipe. The water level gauge is fixedly mounted on a side wall of a middle section of the test water tank and is located at a opposite side of the inlet pipe. The lower end of the upright is fixedly mounted on the bottom end of inner of the test water tank. The clamping device is fixedly mounted on the top end of the upright. The position sensor is fixedly mounted on the inner wall of the test water tank, and has the same installation height as the upright.

An apparatus for measuring a water absorption rate of silane coating on a surface of concrete is disclosed by Chinese patent NO. 201720023957.7, which includes a rectangular testing box with a full opening at the top. A plurality of support rods fixed on a bottom surface are arranged inside the testing box and are used to support concrete specimens. Highest points of all support rods are on the same horizontal plane. An adjusting box with a full opening on the top surface is arranged outside the testing box. The adjusting box has a side surface provided with a discharge port, and another side surface opposite to the side surface and provided with a water inlet. A position of the water inlet is higher than the position of the discharge port. The adjusting box is connected with the testing box via a connecting pipe, which is configured to control a water surface elevation of the testing box. Due to taking and placing the concrete specimen, the water absorption effect of the concrete specimen, and the water evaporation, the water level will be changed. The water level inside the adjusting box is kept constant by filling water through the inlet and discharging water by the outlet, and the water level inside the testing box is kept constant through the connecting pipe.

An instrument for measuring a water absorption rate of a surface of concrete is disclosed by Chinese patent NO. 201720349209.8, which includes a concrete sampling box, a box for measuring water absorption rate, a cover plate, a position regulator, a rubber gasket, an elastic rope, a fastening clip, a water absorption sponge, a water for measuring and a humidity sensor. A rubber gasket is arranged under the box for measuring water absorption rate. The concrete sampling box is arranged outside the box for measuring water absorption rate. The position regulator is arranged on a side surface of the concrete sampling box. The position regulator is connected inwardly with the humidity sensor. The cover plate is arranged above the box for measuring water absorption rate. The elastic rope is arranged on edges of the cover plate. The elastic rope is detachably fixed outside the concrete sampling box by means of a fastening clip. The water absorption sponge is arranged inside the upper part of the box for measuring water absorption rate, and the water for measuring is arranged inside the lower part of the box for measuring water absorption rate.

The inventors find that, due to the constraints of the laboratory conditions, it is difficult to achieve an operation under loading and in a parallel direction of a media transmission direction in the existing technology. Regarding studies of a water absorption performance of concrete under load, most of them only carry out analysis of the water absorption performance after unloading or in a vertical loading direction. The internal cracks and porosity of concrete may be closed after unloading. It may be not reflected really damage condition and properties of medium transmission under actual service conditions. A longitudinal strain and a transverse strain of concrete under loading are quite different. A development of internal cracks and porosity of concrete in a direction parallel to direction of loading is also different from that in a direction perpendicular to direction of loading. In addition, apparatuses for testing water absorption rate of concrete in the existing technology fails to achieve monitoring of water absorption process of the concrete in real time and continuously.

SUMMARY

In view of the deficiencies of the existing technology, the embodiments aim to provide an apparatus and method for testing water absorption of concrete in a direction parallel with load applying direction, which solve a problem of coupling load action with the water absorption of concrete in a direction parallel to a loading direction, and achieve the requirements of high-precision measurement of the capillary water absorption rate of concrete specimen under different loads and simple operation.

In order to achieve the above objectives, the present disclosure is achieved by following technical solutions.

In a first aspect, an apparatus for testing water absorption of concrete in a direction parallel with load applying direction is provided according to an embodiment of the present disclosure, which includes:

a loading device, including an upper support plate and a lower support plate connected with the upper support plate via a plurality of threaded rods, and a space for placing a concrete specimen being formed between the upper support plate and the lower support plate; a top of each threaded rod being connected with a nut through a spring; a plurality of pressing columns being connected under the upper support plate;

a water filling device, including a water filling cylinder sleeved outside the pressing columns, the water filling cylinder having a side connected with a water supply tank via an inlet pipe, and another side connected with a water storage tank via an outlet pipe;

a monitoring device, including a mass sensor arranged under the water storage tank and a strain gauge for detecting change of stress of the concrete specimen; the mass sensor transmitting detected mass information of water flow inside the water storage tank to a computer to calculate the water absorption rate of the concrete specimen.

In a further embodiment, the pressing columns are arranged at even intervals, each pressing column has a first end fixedly connected with the upper support plate, and a second end configured for pressing a water absorption surface of the concrete specimen. The pressing columns are divergently arranged in circular rings with a center of the upper support plate as a center.

In a further embodiment, the water filling cylinder is a reducer, and a top of the water filling cylinder is fixedly connected with the upper support plate via an annular plate.

In a further embodiment, the inlet pipe is equipped with a valve; a diameter of the inlet pipe is greater than a diameter of the outlet pipe. The inlet pipe is connected with a position close to a bottom of the water supply tank, and the water storage tank is connected with the outlet pipe via a hose.

In a further embodiment, the water storage tank has a bottom surface inclined at a set angle.

In a further embodiment manner, the mass sensor and the strain gauge are respectively connected with the computer via a multi-channel data collector.

In a second aspect, a method for testing water absorption of concrete in a direction parallel with load applying direct is provided according to an embodiment of the present disclosure, where the apparatus for testing water absorption rate of concrete is adopted, and the method includes:

sealingly connecting an annular plate with the upper support plate, waterproofing a side surface of the concrete specimen, pasting the strain gauge on a side of the concrete specimen, and connecting the strain gauge to the computer via a multi-channel data collector; connecting the concrete specimen with the annular plate by using the water filling cylinder, and fixing the concrete specimen to the water filling cylinder with a hoop;

connecting the upper support plate with the lower support plate by using the threaded rods, and successively sleeving the spring and the nut to the top of each threaded rod; applying a force to the concrete specimen by means of a press, tightening the nut in a case that the applied force reaching the predetermined stress level is displayed on the computer;

placing the water storage tank on the mass sensor, connecting a hose with the outlet pipe, and connecting the mass sensor to the computer; opening the water filling valve to flow water from the water supply tank to the water storage tank, and closing the water filling valve when increased value of mass of the water storage tank reaches a set amount; once stopping filling the water, turning on a timer and monitoring reduction amount of the mass of the water storage tank in real time by means of the computer.

In a further embodiment, a bottom surface of the water storage tank is higher than a bottom surface of the upper support plate by a set distance; in a process of filling the water, a water level line inside the water supply tank is kept higher than the bottom surface of the water storage tank by a set distance.

The beneficial effects of the above embodiments of the present disclosure are as follows:

1. In one or more embodiments of the present disclosure, several pressing columns are configured to load the concrete specimen to realize the test of water absorption rate of concrete in a direction parallel to a loading direction. While continuous load is applied, surface water absorption rate of the concrete in a direction parallel to the loading direction is measured, which can solve a problem of coupling load action with the water absorption of concrete in a direction parallel to the loading direction, and lay the foundation for studying the influence mechanism and change regular of water absorption of the concrete in a direction parallel to the loading direction.

2. In one or more embodiments of the present disclosure, the force is transmitted between the upper support plate and the nuts by means of the springs. In this way, the stress loss caused by a buckling of the concrete specimen can be reduced. The strain gauge adhered on the concrete specimen may monitor a stress level of the concrete specimen in real time, and may ensure that the stress is in the target state by adjusting the nuts in time when the stress is lost.

3. In one or more embodiments of the present disclosure, the mass sensor is connected with the computer. A change regular of the reduction amount of mass of the water storage tank and time may be transmitted to the computer in real time to plot a cumulative water absorption amount curve of the concrete specimen in real time, and thus errors caused by artificial readings can be reduced.

4. In one or more embodiments of the present disclosure, the annular plate is connected with the concrete speciment via a hoop and a water filling cylinder, which is simple to operate and can be reused. The water storage tank is placed on the mass sensor to test a capillary water absorption amount of the concrete specimen in real time and continuously. In this way, the high-precision measurement of the capillary water absorption rate of concrete specimen can be achieved under different loads. The structure is simple, and the operation is simple.

BRIEF DESCRIPTION OF THE DRAWINGS

The accompanying drawings constituting a part of the present disclosure are used to provide a further understanding of the present disclosure. The exemplary embodiments and descriptions of the present disclosure are used for explaining the present disclosure, and do not limit the present disclosure.

Figure 1:
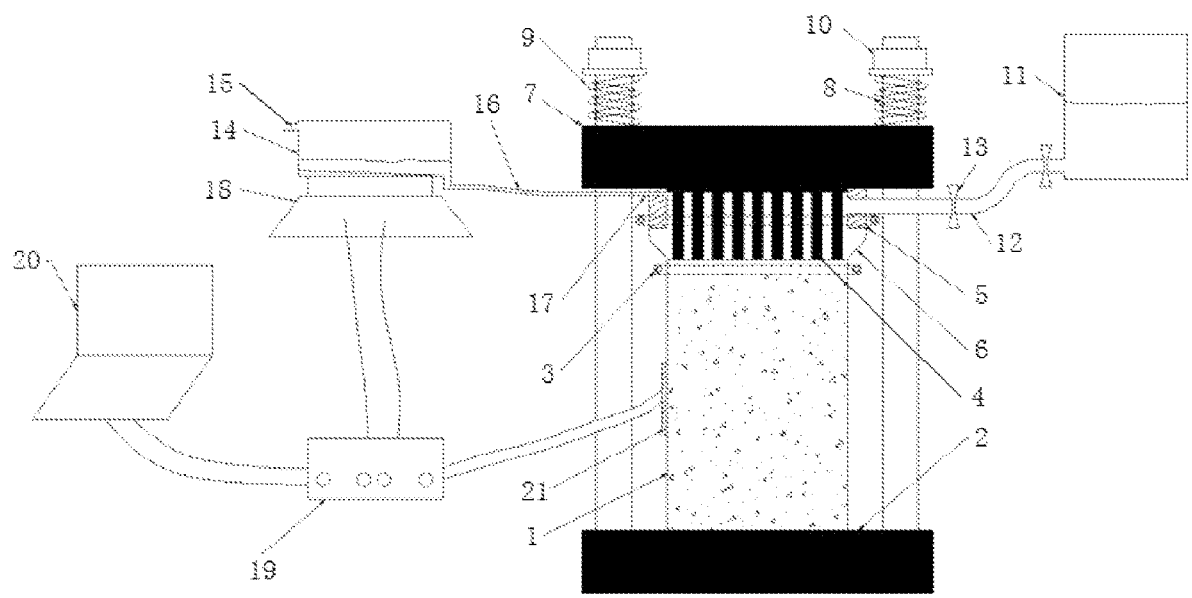
FIG. 1 is a schematic structural diagram according to one or more embodiments of the disclosure.
Figure 2:
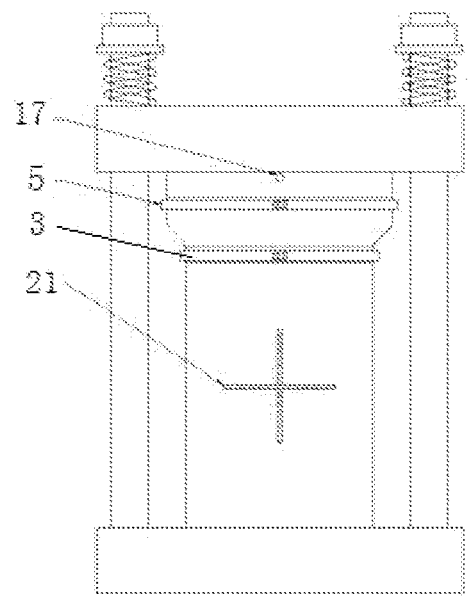
FIG. 2 is a schematic structural diagram of a loading device according to one or more embodiments of the present disclosure.

Where, 1 concrete specimen, 2 lower support plate, 3 hoop, 4 pressing columns, 5 annular plate, 6 water filling cylinder, 7 upper support plate, 8 threaded rods, 9 springs, 10 nuts, 11 water supply tank, 12 inlet pipe, 13 valve, 14 water storage tank, 15 air pressure balance hole, 16 hose, 17 outlet pipe, 18 mass sensor, 19 multi-channel data collector, 20 computer, 21 strain gauge.

In the figures, distances or sizes between parts is exaggerated to show position of each part, and the schematic diagram is only for illustration.

DETAILED DESCRIPTION OF EMBODIMENTS

It should be noted that a following detailed description is exemplary, and is intended to provide further description of the present application. Unless otherwise specified, all technical and scientific terms used herein have the same meaning as commonly understood by those of ordinary skill in the art to which this application belongs.

It should be noted that the terms used herein are only for describing particular embodiments and are not intended to limit exemplary embodiments according to the present application. As used herein, unless the context clearly indicates otherwise, singular form is also intended to include plural form. In addition, it should also be understood that the terms "comprise" and/or "include", when used in this description, indicate features, steps, operations, devices, components and/or combinations thereof.

The term explanation section: the terms in the present application, such as "mount", "connect . . . with", "connect" and "fix", should be understood broadly. For example, it may be a fixed connection, a detachable connection, or an integral connection. It may be a direct connection, or an indirect connection via an intermediate medium, and may be an internal connection of two elements, or an interactive relationship between two elements. For those of ordinary skill in the art, the above terms can be understood in the specific meaning of the present disclosure according to specific situations.

Embodiment 1

The present disclosure is described in detail below in combination with FIGS. 1-4, and specifically, structure is as follows.

An apparatus for testing water absorption of concrete in a direction parallel with load applying direction is provided according to the present embodiment. The apparatus includes a loading device, a water filling device and a monitoring device. The loading device is configured to apply pressure to a concrete specimen 1. The water filling device is used to supply water used for a water absorption test of the concrete specimen 1. The monitoring device is configured to measure data in real time.

The loading device includes a lower support plate 2, an upper support plate 7, pressing columns 4, threaded rods 8, springs 9 and nuts 10. The upper support plate 7 and the lower support plate 2 are connected by means of a plurality of threaded rods 8, to form a space for placing the concrete specimen 1 between the upper support plate 7 and the lower support plate 2.

A part of each threaded rod 8 extending out of a top of the upper support plate 7 is mounted with a nut 10. The spring 9 are arranged between the nut 10 and the upper support plate 7, and are sleeved outside the threaded rod 8. The spring 9 applies forces to the upper support plate 7 by rotating the nut 10, and the forces is transmitted between the upper support plate 7 and the nut 10 via the spring 9. In this way, the stress loss caused by a creep of the concrete specimen 1 can be reduced.

Figure 3:
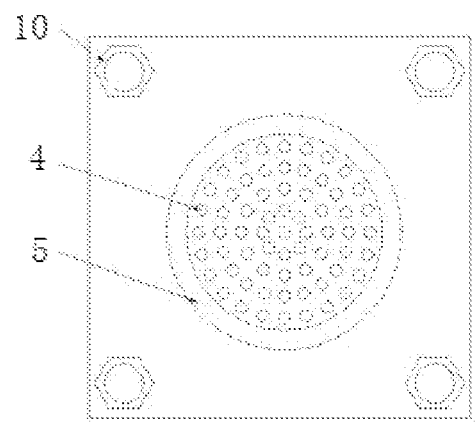
FIG. 3 is a top view of a loading device according to one or more embodiments of the present disclosure.
Figure 4:
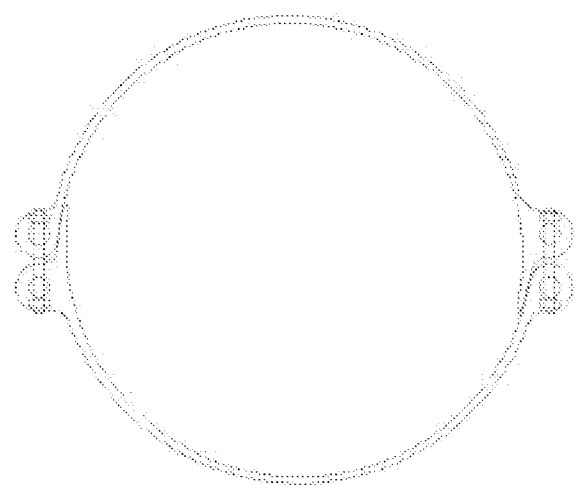
FIG. 4 is a schematic structural diagram of a hoop according to one or more embodiments of the present disclosure.

In an embodiment, both the upper support plate 7 and the lower support plate 2 are rectangular steel plates. As shown in FIG. 3, there are four threaded rods 8, which are respectively located at positions near four corners of the upper support plate 7 and the lower support plate 2. It can be understood that the upper support plate 7 and the lower support plate 2 may also be other shapes and other metal plates. The threaded rods 8 may also be other numbers, which may be specifically selected according to actual requirements of test.

Multiple pressing columns 4 are fixed on a lower surface of the upper support plate 7, and are integrally connected with the upper support plate 7. The pressing columns 4 are arranged uniformly at intervals. The thickness of the upper support plate 7 and the lower support plate 2 are the same, both of which are 20-50 mm. In this way, each of the pressing columns 4 is subjected to the same force. In an embodiment, the pressing columns 4 are divergently arranged in circular rings with a center of the upper support plate 7 as a center. When the upper support plate 7 is moved downward, pressure is applied to the concrete specimen 1 via the pressing columns 4, so as to realize a test of water absorption amount of the concrete in a direction parallel to a loading direction. In the embodiment, the pressing columns 4 are stainless steel columns.

The water filling device includes a water supply tank 11, a water filling cylinder 6 and a water storage tank 14. The water filling cylinder 6 is sleeved outside the pressing columns 4, and an inner wall of the water filling cylinder 6 has a distance from an outermost pressing columns 4. The water filling cylinder 6 is a reducer made of silicone. A larger diameter end of the water filling cylinder 6 is fixed to a bottom of the upper support plate 7 by means of an annular plate 5, and a smaller diameter end of the water filling cylinder 6 is fixed to the concrete specimen 1. In a test process, the concrete specimen 1 is vertically placed in the space between the upper support plate 7 and the lower support plate 2, a top of the concrete specimen 1 is fixed with the water filling cylinder 6 via a hoop 3, and the pressing columns 4 are in contact with a top surface of the concrete specimen 1.

An inlet port is provided on one side of water filling cylinder 6 and an outlet port is provided on another side of water filling cylinder 6. The outlet port is equipped with a outlet pipe 17. The water supply tank 11 is in communication with the inlet port via an inlet pipe 12, and the inlet pipe 12 is equipped with a valve 13. The valve 13 is opened, and water of the water supply tank 11 enters into the water filling cylinder 6 through the inlet pipe 12, so that the water enters into the concrete specimen 1 from the top surface thereof. The inlet pipe 12 is connected with a position close to a bottom of the water supply tank 11, so as to smooth the water in the water supply tank 11 into the water filling cylinder 6.

The water storage tank 14 is connected with the outlet pipe 17 via a hose 16, and the hose 16 is connected with a position close to a bottom of the water storage tank 14. When the water filling amount is greater than the water absorption amount of the concrete specimen 1, the water enters into the water storage tank 14 through the outlet pipe 17, and the water absorption rate of the concrete specimen 1 is determined by obtaining a mass of the water storage tank 14. In the present embodiment, a material of the hose 16 is silicone.

The water storage tank 14 is a square structure, such as a cube structure. The water storage tank 14 has an inner bottom surface inclined at a set angle. In an embodiment, an inclination angle of the inner bottom surface of the water storage tank 14 is 2 degrees. The inner bottom surface of the water storage tank 14 is 1-2 mm higher than the bottom surface of the upper support plate 7, so as to ensure sufficient reflow of water. An air pressure balance hole 15 is provided on one side of the water storage tank 14.

A diameter of the inlet pipe 12 is greater than a diameter of the outlet pipe 17, so that the water supply tank 11 is quickly filled with the water, which reduces an influence of short-term water absorption of the concrete specimen 1 on the subsequent measurement result during water filling. In the present embodiment, an outer diameter and inner diameter of the inlet pipe 12 are 10-15 mm and 8-13 mm, respectively. An outer diameter and inner diameter of the outlet pipe 17 are 3-25 mm and 2-4 mm, respectively.

The monitoring device includes a mass sensor 18, a multi-channel data collector 19, a computer 20 and a strain gauge 21. The mass sensor 18 is arranged under the water storage tank 14. The mass sensor 18 is electrically connected with the multi-channel data collector 19. The multi-channel data collector 19 is electrically connected with the computer 20 and the strain gauge 21 adhered to a side surface of the concrete specimen 1, respectively.

The multi-channel data collector 19 is a data collecting product with USB interface, and may be connected with various desktop computers, notebooks, and industrial computers with USB interfaces to form a high performance data collecting and measurement system. The computer 20 stores therein a program capable of writing and recording a relationship between the reduction amount of mass of the water storage tank 14 and time. In the present embodiment, the mass sensor 18 with a range of 0 to 500 g and an accuracy of 0.01 g is selected. The strain gauge 21 is a resistance strain gauge.

Embodiment 2

A method for testing water absorption of concrete in a direction parallel with load applying direction is provided according to an embodiment. The method may include the following steps.

An annular plate 5 is sealingly connected with an upper support plate 7 by using building structure glues. A waterproof treatment of a side surface of a concrete speciment 1 by using an epoxy resin. The concrete specimen 1 has a bottom surface diameter of 100 mm and a height of 150 mm, and the strain gauge 21 is adhered to a side of the concrete specimen 1. A strain gauge 21 is connected with the computer 20 via a multi-channel data collector 19. The concrete specimen 1 is connected with the annular plate 5 by using the water filling cylinder 6, and the water filling cylinder 6 is clamped and sealed with the hoop 3.

The upper support plate 7 and the lower support plate 2 are connected by using threaded rods 8, and the springs 9 and the nuts 10 are successively sleeved the top ends of the threaded rods 8. A force is applied to the concrete specimen 1 by means of a press, the nuts 10 above the springs 9 is tightened when the computer shows a predetermined stress level applied on the concrete specimen 1.

The water storage tank 14 is placed on the mass sensor 18, and the bottom surface of the water storage tank 14 is 1-2 mm higher than the bottom surface of the upper support plate 7. The hose 16 is connected with the outlet pipe 17. The mass sensor 18 is connected with the computer 20.

The water filling valve 13 is opened, and the water in the water supply tank 11 flows into the water storage tank 14 through the inlet pipe 12, the water filling cylinder 6 and the outlet pipe 17. When an increased mass of the water storage tank 14 reaches 220-280 g, the water filling valve 13 is closed. During filling the water, a water level line inside the water supply tank 11 is kept higher than the bottom surface of the water storage tank 14 by 10-15 mm. After filling the water is stopped, a timer is turned on, a program for recording a relationship between reduction amount of mass of the water storage tank 14 and time is run in the computer 20 to record an initial mass of the water storage tank 14. The computer 20 monitors reduction amount of mass of the water storage tank 14 in real time.

The computer 20 records the change regular of reduction amount of the mass of the water storage tank 14 over time. A value of reduction amount of the mass of the water storage tank 14 is equal to a value of the water absorption amount of the concrete specimen 1 in a direction parallel to a loading direction. The computer 20 performs data processing on the change regular of the reduction amount of the mass of the water storage tank 14 over time, and plots the cumulative water suction amount curve of the concrete specimen 1 in the direction parallel to the loading in real time.

The above description is merely preferred embodiments of the present application, and is not intended to limit the present application. For those skilled in the art, the present application has various modification and changes. Any modifications, equivalent replacements and improvements and so on made within the spirit and principle of the present application shall all fall within the protection scope of the present application.

What is claimed is:

1. An apparatus for testing water absorption of concrete in a direction parallel with a load applying direction, comprising:
    a loading device, comprising an upper support plate and a lower support plate connected with the upper support plate via a plurality of threaded rods, and a space for placing a concrete specimen being formed between the upper support plate and the lower support plate, a top of each threaded rod being connected with a nut through a spring, a plurality of pressing columns being connected under the upper support plate;
    a water filling device, comprising a water filling cylinder sleeved outside the pressing columns, the water filling cylinder having a side connected with a water supply tank via an inlet pipe, and another side connected with a water storage tank via an outlet pipe; and
    a monitoring device, comprising a mass sensor arranged under the water storage tank and a strain gauge for detecting change of stress of the concrete specimen, the mass sensor configured for transmitting detected mass information of water flow inside the water storage tank to a computer to calculate the water absorption rate of the concrete specimen.

2. The apparatus for testing water absorption of concrete in the direction parallel with the load applying direction according to claim 1, wherein the pressing columns are arranged at even intervals, each pressing column has a first end fixedly connected with the upper support plate, and a second end configured for pressing a water absorption surface of the concrete specimen.

3. The apparatus for testing water absorption of concrete in the direction parallel with the load applying direction according to claim 1, wherein the pressing columns are divergently arranged in circular rings with a center of the upper support plate as a center.

4. The apparatus for testing water absorption of concrete in the direction parallel with the load applying direction according to claim 1, wherein the water filling cylinder is a reducer, and a top of the water filling cylinder is fixedly connected with the upper support plate via an annular plate.

5. The apparatus for testing water absorption of concrete in the direction parallel with the load applying direction according to claim 1, wherein the inlet pipe is equipped with a valve; a diameter of the inlet pipe is greater than a diameter of the outlet pipe.

6. The apparatus for testing water absorption of concrete in the direction parallel with the load applying direction according to claim 1, wherein the water storage tank has a bottom surface inclined at a set angle.

7. The apparatus for testing water absorption of concrete in the direction parallel with the load applying direction according to claim 1, wherein the inlet pipe is connected with a position close to a bottom of the water supply tank, and the water storage tank is connected with the outlet pipe via a hose.

8. The apparatus for testing water absorption of concrete in the direction parallel with the load applying direction according to claim 1, wherein the mass sensor and the strain gauge are respectively connected with the computer via a multi-channel data collector.

9. A method for testing water absorption of concrete in a direction parallel with a load applying direction, using an apparatus for testing water absorption rate of concrete including:
    a loading device, comprising an upper support plate and a lower support plate connected with the upper support plate via a plurality of threaded rods, and a space for placing a concrete specimen being formed between the upper support plate and the lower support plate, a top of each threaded rod being connected with a nut through a spring, a plurality of pressing columns being connected under the upper support plate,
    a water filling device, comprising a water filling cylinder sleeved outside the pressing columns, the water filling cylinder having a side connected with a water supply tank via an inlet pipe, and another side connected with a water storage tank via a water outlet pipe,
    a multi-channel data collector, and
    a monitoring device, comprising a mass sensor arranged under the water storage tank and a strain gauge for detecting change of stress of the concrete specimen, the mass sensor configured for transmitting detected mass information of water flow inside the water storage tank to a computer to calculate the water absorption rate of the concrete specimen, the method comprising:
    sealingly connecting an annular plate with the upper support plate, waterproofing a side surface of the concrete specimen, pasting the strain gauge on a side of the concrete specimen, and connecting the strain gauge to the computer via the multi-channel data collector, connecting the concrete specimen with the annular plate by using the water filling cylinder, and fixing the concrete specimen to the water filling cylinder with a hoop;
    connecting the upper support plate with the lower support plate by using the threaded rods, and successively sleeving the spring and the nut to the top of each threaded rod, applying a force to the concrete specimen by means of a press, tightening the nuts in a case that the applied force reaching a predetermined stress level is displayed on the computer; and
    placing the water storage tank on the mass sensor, connecting a hose with the water outlet pipe, and connecting the mass sensor to the computer, opening the water filling valve to flow water from the water supply tank to the water storage tank, and closing the water filling valve when increased value of mass of the water storage tank reaches a set amount, once stopping filling the water, turning on a timer and monitoring reduction amount of mass of the water storage tank in real time by means of the computer.

10. The method for testing water absorption of concrete in the direction parallel with the load applying direction according to claim 9, wherein:
a bottom surface of the water storage tank is higher than a bottom surface of the upper support plate by a set distance; and
in a process of filling the water, a water level line inside the water supply tank is kept higher than the bottom surface of the water storage tank by a set distance.

11. The method for testing water absorption of concrete in the direction parallel with the load applying direction according to claim 9, wherein the pressing columns are arranged at even intervals, each pressing column has a first end fixedly connected with the upper support plate, and a second end configured for pressing a water absorption surface of the concrete specimen.

12. The method for testing water absorption of concrete in the direction parallel with the load applying direction according to claim 9, wherein the pressing columns are divergently arranged in circular rings with a center of the upper support plate as a center.

13. The method for testing water absorption of concrete in the direction parallel with the load applying direction according to claim 9, wherein the water filling cylinder is a reducer, and a top of the water filling cylinder is fixedly connected with the upper support plate via an annular plate.

14. The method for testing water absorption of concrete in the direction parallel with the load applying direction according to claim 9, wherein the inlet pipe is equipped with a valve and a diameter of the inlet pipe is greater than a diameter of the outlet pipe.

15. The method for testing water absorption of concrete in the direction parallel with the load applying direction according to claim 9, wherein the water storage tank has a bottom surface inclined at a set angle.

16. The method for testing water absorption of concrete in the direction parallel with the load applying direction according to claim 9, wherein the inlet pipe is connected with a position close to a bottom of the water supply tank, and the water storage tank is connected with the outlet pipe via a hose.

17. The method for testing water absorption of concrete in the direction parallel with the load applying direction according to claim 9, wherein the mass sensor and the strain gauge are respectively connected with the computer via a multi-channel data collector.

\* \* \* \* \*